United States Patent
Taff et al.

(10) Patent No.: US 10,799,707 B2
(45) Date of Patent: Oct. 13, 2020

(54) ENHANCED THERAPY SETTINGS IN PROGRAMMABLE ELECTROSTIMULATORS

(71) Applicant: BIOTRONIK SE & CO. KG, Berlin (DE)

(72) Inventors: Brian M. Taff, Portland, OR (US); Kurt Swenson, Dayton, OR (US); Hannes Kraetschmer, West Linn, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 228 days.

(21) Appl. No.: 15/804,017

(22) Filed: Nov. 6, 2017

(65) Prior Publication Data

US 2018/0133490 A1  May 17, 2018

Related U.S. Application Data

(60) Provisional application No. 62/423,211, filed on Nov. 17, 2016.

(51) Int. Cl.
  *A61N 1/37* (2006.01)
  *A61N 1/372* (2006.01)
  (Continued)

(52) U.S. Cl.
  CPC ......... *A61N 1/37247* (2013.01); *A61N 1/025* (2013.01); *A61N 1/08* (2013.01);
  (Continued)

(58) Field of Classification Search
  CPC ............ A61N 1/37247; A61N 1/36142; A61N 1/378; A61N 1/025; A61N 1/08;
  (Continued)

(56) References Cited

U.S. PATENT DOCUMENTS

| | | | |
|---|---|---|---|
| 7,149,573 B2 * | 12/2006 | Wang ................... | A61B 5/053 600/547 |
| 8,942,819 B2 | 1/2015 | Hincapie Ordonez et al. | |

(Continued)

FOREIGN PATENT DOCUMENTS

| | | |
|---|---|---|
| WO | 2009076211 A1 | 6/2009 |
| WO | 2009079600 A1 | 6/2009 |

(Continued)

OTHER PUBLICATIONS

Robert V. Shannon; "A Model of Safe Levels for Electrical Stimulation"; IEEE Transactions on Biomedical Engineering; Apr. 1992; pp. 424-426; vol. 39, No. 4. IEEE.

*Primary Examiner* — Amanda K Hulbert
*Assistant Examiner* — Natasha Patel
(74) *Attorney, Agent, or Firm* — Laurence A. Greenberg; Werner H. Stemer; Ralph E. Locher

(57) ABSTRACT

In an electrostimulator which applies electrical stimulation to patient tissue, measurements of lead impedance (tissue resistance), battery status, and like matters are used to format and/or truncate the ranges of programmable therapeutic output settings available for selection by a clinician. The clinician can therefore better tell whether chosen settings can actually be successfully implemented, and/or whether they may have adverse effects on device lifespan or patient safety.

19 Claims, 3 Drawing Sheets

(51) Int. Cl.
  *A61N 1/08*  (2006.01)
  *A61N 1/02*  (2006.01)
  *A61N 1/378*  (2006.01)
  *A61N 1/36*  (2006.01)
  *A61N 1/05*  (2006.01)
  *A61N 1/39*  (2006.01)
  *A61N 1/365*  (2006.01)

(52) U.S. Cl.
  CPC ......... *A61N 1/36142* (2013.01); *A61N 1/378* (2013.01); *A61N 1/0556* (2013.01); *A61N 1/0563* (2013.01); *A61N 1/36053* (2013.01); *A61N 1/36062* (2017.08); *A61N 1/36071* (2013.01); *A61N 1/36521* (2013.01); *A61N 1/3956* (2013.01)

(58) Field of Classification Search
  CPC .............. A61N 1/3956; A61N 1/36521; A61N 1/36071; A61N 1/36053; A61N 1/0563; A61N 1/0556; A61N 1/36062
  See application file for complete search history.

(56) References Cited

U.S. PATENT DOCUMENTS

| | | |
|---|---|---|
| 9,205,263 B2 | 12/2015 | King et al. |
| 9,452,288 B2 | 9/2016 | Whitehurst et al. |
| 9,744,365 B2 | 8/2017 | Davis et al. |
| 9,750,939 B2 | 9/2017 | Carcieri et al. |
| 2007/0191901 A1* | 8/2007 | Schecter ............. A61N 1/3627 607/17 |
| 2009/0157155 A1 | 6/2009 | Bradley |
| 2014/0288620 A1* | 9/2014 | DiLorenzo ......... A61N 1/36053 607/62 |
| 2015/0165205 A1* | 6/2015 | Rockweiler ........ A61N 1/37247 607/28 |
| 2015/0258341 A1 | 9/2015 | Ternes et al. |
| 2017/0001011 A1* | 1/2017 | An ...................... A61N 1/3684 |

FOREIGN PATENT DOCUMENTS

| | | |
|---|---|---|
| WO | 2011085232 A1 | 7/2011 |
| WO | 2016172239 A1 | 10/2016 |

* cited by examiner

FIG. 2

ENHANCED THERAPY SETTINGS IN PROGRAMMABLE ELECTROSTIMULATORS

CROSS-REFERENCE TO RELATED APPLICATION

This application claims the priority, under 35 U.S.C. § 119(e), of provisional patent application No. 62/423,211 filed Nov. 17, 2016; the prior application is herewith incorporated by reference in its entirety.

BACKGROUND OF THE INVENTION

Field of the Invention

This document concerns an invention relating generally to medical therapies wherein electrical stimulation is applied to a patient, and more specifically to the programming of electrostimulators used in such therapies.

Numerous medical therapies apply electrical stimulation to the body to treat or relieve disorders. As an example, implantable cardioverter defibrillators (ICDs) are electrostimulators which apply electrical stimulation to the heart muscles to treat arrhythmia. As another example, implantable pulse generators (IPGs) are electrostimulators which apply electrical stimulation to spinal or peripheral nerves to block or stimulate nerve signals, and thereby modify the nerve-driven behavior of body tissue. Examples of neurostimulation include spinal cord stimulation (SCS), which can at least partially block chronic pain, and vagus nerve stimulation (VNS), which can treat congestive heart failure (CHF).

Physicians and other programmers typically program (configure) an electrostimulator to apply appropriate therapies to a patient using any one of a variety of programming devices, which can vary in form from conventional personal computers to specially-configured hand-held electronic tablets or the like. The programming device provides the programmer-specified therapy instructions to the electrostimulator via wireless or wired communications. During programming, the programming device typically visually depicts electrostimulation parameters such as stimulation pulse amplitude, stimulation pulse width (pulse duration), stimulation pulse frequency, pulse burst frequency (a pulse burst being a "train" of stimulation pulses), pulse quantity per pulse burst, and the like. The programmer may be able to select values for some or all of these parameters, and/or may be presented with predefined sets of values for selection. Each selectable set of values represents a "stimulation vector" defining a possible stimulation therapy that can be applied to the patient. Thus, once a programmer selects or defines a stimulation vector (or vectors), the programming device transmits the vector(s) to the electrostimulator, which then delivers stimulation therapy to the patient wherein the stimulation is defined by the vector(s).

Programmers often encounter difficulties when programming an electrostimulator to apply appropriate therapy to a patient. First, the stimulation vector as chosen or specified by the programmer may not correspond to the one actually delivered by the electrostimulator. As an example, it is well known that lead impedance—that is, the electrical resistance encountered by a stimulation pulse as it travels through an electrostimulator's lead to an electrode in contact with patient tissue, and as it flows into tissue—can change over time owing to scar tissue formation, movement of the electrode-bearing lead, and/or changes in patient posture. This is usually not a significant problem for electrostimulators that primarily define their therapies using voltage-based stimulation vectors, as the specified voltages can typically be delivered across patient tissue regardless of the tissue's electrical resistance. However, this can be a significant problem for electrostimulators that primarily define their therapies using current-based stimulation vectors. If a programmed stimulation vector calls for delivery of high current, and lead impedance is high, the electrostimulator will need a high driving voltage to provide the specified current. This driving voltage may be beyond the performance limits of the electrostimulator's battery and/or circuitry, and thus the electrostimulator may be incapable of providing the specified stimulation vector. This leads to the problem that the range of selectable stimulation vectors displayed to a programmer may not correspond to the stimulation vectors that can practically be delivered by the electrostimulator.

Second, even where all stimulation vectors displayed by a programming device are in fact deliverable by the electrostimulator, the display may not fully convey to the programmer the ramifications of his/her selection. As an example, some stimulation vectors may approach or exceed patient safety margins. In the field of neurostimulation, the so-called "Shannon criteria" (R. V. Shannon, "A Model of Safe Levels for Electrical Stimulation," *IEEE Transactions on Biomedical Engineering* 39 (4): 424-426 (April 1992)) are often used to define patient safety margins beyond which stimulation vectors can damage nervous tissue. As another example, some stimulation vectors may have a significant adverse effect on the electrostimulator's battery life. This can be problematic for an implanted electrostimulator because battery replacement may require explantation and re-implantation of the electrostimulator.

Prior patents illustrate approaches for addressing some of the foregoing problems. U.S. Pat. No. 8,942,819 discusses an electrostimulator wherein "safe" sets of stored stimulation vectors (e.g., stimulation vectors which meet the Shannon criteria) are stored in the electrostimulator's memory. The electrostimulator occasionally performs a "titration sweep," that is, a closed-loop optimization of stimulation vectors, wherein the stimulation vectors are each implemented in succession on the patient. The patient's physiological response to each vector (e.g., cardiac activity) is measured by the electrostimulator and compared to a stored target range. The electrostimulator adjusts stimulation vectors based on the comparison, and attempts to keep the response within the target range.

U.S. Pat. No. 9,205,263 describes an electrostimulator which monitors its electrodes' effectiveness at delivering neural stimulation by monitoring lead impedance, and which adapts the stimulation to compensate for increases and/or decreases in effectiveness.

SUMMARY OF THE INVENTION

The invention, which is defined by the claims set forth at the end of this document, is directed to electrostimulators, and methods of programming electrostimulators, which at least partially alleviate the aforementioned problems. A basic understanding of some of the features of exemplary versions of the invention can be attained from a review of the following brief summary of the invention, with more details being provided elsewhere in this document. To assist in the reader's understanding, the following review makes occasional reference to the accompanying drawings (which are briefly reviewed in the "Brief Description of the Drawings" section following this Summary section of this document).

A preferred version of the invention involves an electrostimulator (for example, the exemplary neurostimulator 100 of FIG. 1) having a lead 102 with an electrode 104 thereon; a battery 106; and a controller 108 configured to deliver electrostimulation from the battery 106 to patient tissue via the electrode 104, with the delivered electrostimulation being defined by a selected one of several available stimulation vectors. Each stimulation vector includes, and is effectively defined by, stimulation parameters. For example, where the electrostimulator is an IPG used for neurostimulation, the stimulation parameters defining a stimulation vector may include stimulation pulse amplitude, stimulation pulse width, stimulation pulse frequency, pulse burst frequency, and pulse quantity per pulse burst. Other parameters are possible as well.

After (or while) the electrostimulator 100 delivers electrostimulation using the selected stimulation vector, the lead impedance of the electrostimulator lead 102 is measured. A status vector is then calculated for each of the several available stimulation vectors, with each status vector representing the effect of delivering electrostimulation at the measured lead impedance, and using the stimulation vector corresponding to the status vector. The status vector may include one or more parameters such as patient safety margins, electrostimulator battery life, and electrostimulator performance limits. In effect, whereas the stimulation vectors represent stimulation therapies displayed to the programmer for selection, the status vectors represent the consequences if the stimulation vectors were actually implemented during patient therapy.

At least some of the several available stimulation vectors are then visually displayed to the programmer for selection (e.g., on the exemplary programming device 150 of FIG. 1), with the visual appearance of the display being dependent on the status vectors. As an example, stimulation vectors having both acceptable and unacceptable status vectors might be displayed to the programmer along with acceptability indicia, wherein the acceptability indicia visually differentiate the displayed stimulation vectors having acceptable status vectors from the displayed stimulation vectors having unacceptable status vectors. A simple example is shown in FIG. 2, depicting a display 200 of selectable stimulation vectors 202, 204, etc. having 0.2 mA, 0.4 mA, 0.6 mA, etc. pulse amplitudes, and with each stimulation vector being shown with acceptability indicia indicating the stimulation vector's patient safety margin (at 206), impact on electrostimulator battery life (at 208), and hardware compatibility (at 210). As can be seen, as pulse amplitude increases, the associated acceptability indicia indicating safety margin changes to indicate danger; the associated acceptability indicia indicating battery impact changes to indicate decreased battery life; and the associated acceptability indicia indicating hardware compatibility changes from a compatibility indication, to an indication that the stimulation vector might be implemented with compromises, to an indication that the electrostimulator cannot support the stimulation vector at all.

Alternatively, only those stimulation vectors having acceptable status vectors might be displayed. FIG. 3 illustrates an exemplary display 300 of this nature, wherein only safe and viable stimulation vectors are shown along with an indication of how near each stimulation vector is to the limits of the electrostimulator's abilities (here a 7.5 mA maximum output current); how near each stimulation vector is to a patient safety threshold (here a Shannon k value of 1.5, beyond which nerve damage might occur); and the impact of each stimulation vector on battery life. Preferably, where the invention displays to a programmer only those stimulation vectors having acceptable status vectors, it does so by displaying those stimulation vectors at the bounds of acceptability, with the programmer having the option of selecting any stimulation vectors within these bounds. The measured lead impedance might also be displayed to the programmer along with the stimulation vectors, as the lead impedance can itself convey information regarding the efficacy of stimulation.

The foregoing steps are preferably periodically repeated (either automatically or via triggering from the programmer or other sources), with lead impedance measurements periodically being updated; with status vectors being updated for the available stimulation vectors; and with the display of the stimulation vectors being updated to account for any changes in the status vectors. The programmer is thereby presented with a menu of stimulation vectors for selection, with the menu presenting current (or at least recent) information regarding the impact of implementing the displayed stimulation vectors. The programmer is thereby assisted in choosing and implementing appropriate electrostimulation therapy, particularly inasmuch as it helps educate the programmer of the trade-offs that occur with selection of different stimulation vectors.

The foregoing steps are preferably performed in a system including an electrostimulator and a programming device, with the electrostimulator providing the electrostimulation and lead impedance measurement functions, and the programming device providing the display of the stimulation vectors, and also allowing the programmer's choice or definition of the stimulation vectors. The determination of the status vectors can be provided in the electrostimulator, in the programming device, or in both of these components. Owing to the interdependence of the electrostimulator and its programming device, where the term "electrostimulator" is used throughout this document, it should generally be understood as meaning an electrostimulator either alone or in conjunction with a compatible programming device, unless the context of the term's use indicates otherwise.

The invention is particularly beneficial in neurostimulation applications, most particularly in neurostimulators used for VNS or SCS. Moreover, the invention is particularly beneficial in electrostimulators that deliver current-based stimulation, that is, in electrostimulators that deliver electrostimulation having a defined current regardless of the voltage at which the defined current is delivered.

Further advantages, features, and objects of the invention will be apparent from the remainder of this document in conjunction with the associated drawings.

Other features which are considered as characteristic for the invention are set forth in the appended claims.

Although the invention is illustrated and described herein as embodied in an enhanced therapy settings in programmable electrostimulators, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 2 is a diagram of a simple exemplary graphical user interface (GUI) that might be displayed on the screen of a programming device to allow a programmer to choose a desired stimulation vector.

DETAILED DESCRIPTION OF THE INVENTION

Expanding on the discussion above, preferred forms of the invention provide feedback to the programmer which helps to ensure that programmed therapy better reflects actual delivered therapy, and that proposed therapy programs can be properly evaluated in light of possible electrostimulator limitations and patient safety/comfort considerations.

Figure 1:
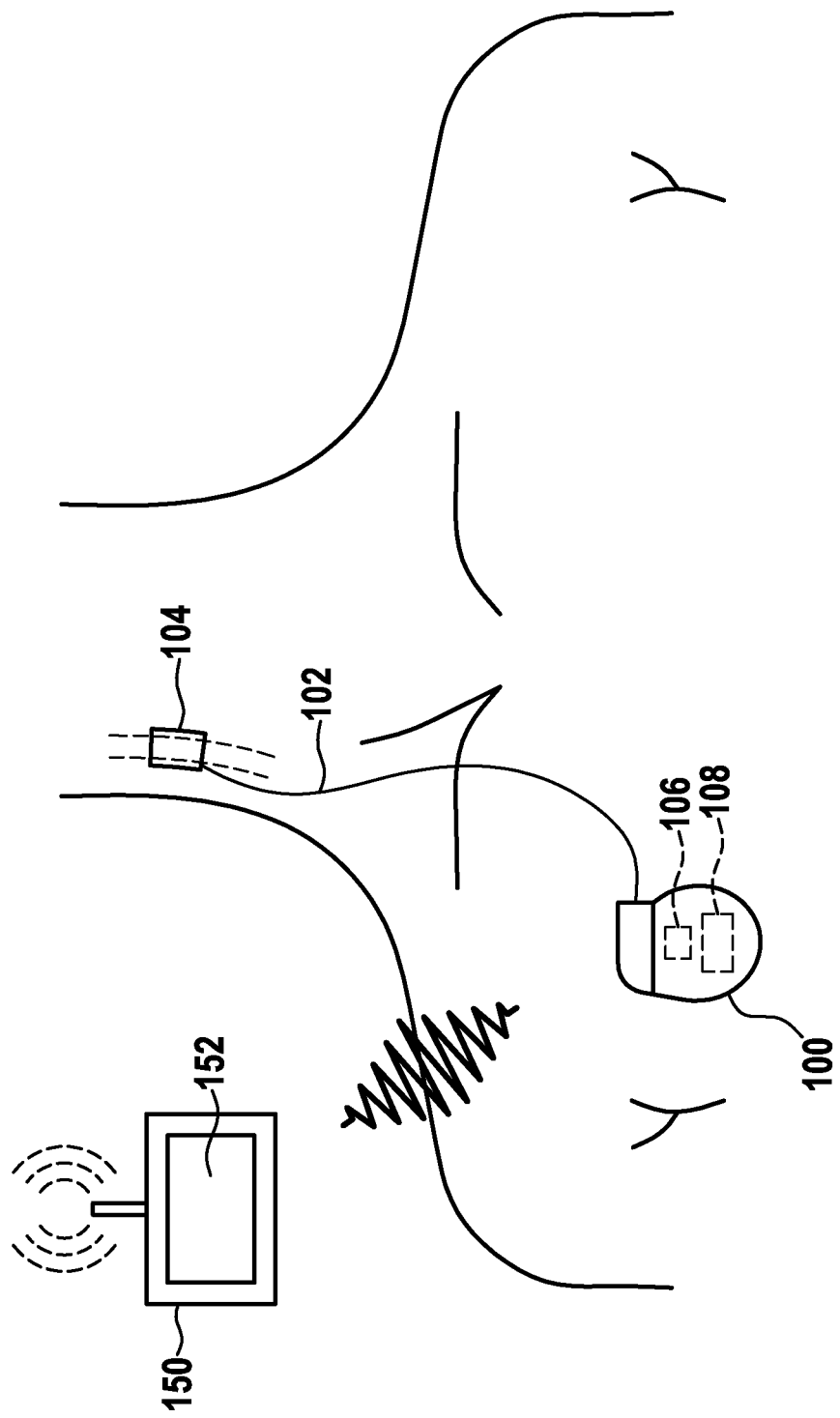
FIG. 1 is a simplified schematic diagram of an electrostimulator (here a neurostimulator) implanted within a patient, shown with a programming device for wirelessly transmitting therapy programming to the electrostimulator.

To review the aforementioned FIG. 1 in greater detail, this image depicts an electrostimulator 100, here a neurostimulator, implanted within a patient's body, along with a programming device 150 configured to wirelessly communicate programming to the electrostimulator 100. The controller 108 of the electrostimulator 100 stores this programming, and delivers the stimulation prescribed by the programming to the patient via the electrostimulator lead 102 and its electrode 104 (here shown as a cuff electrode situated about the vagus nerve).

Figure 2:
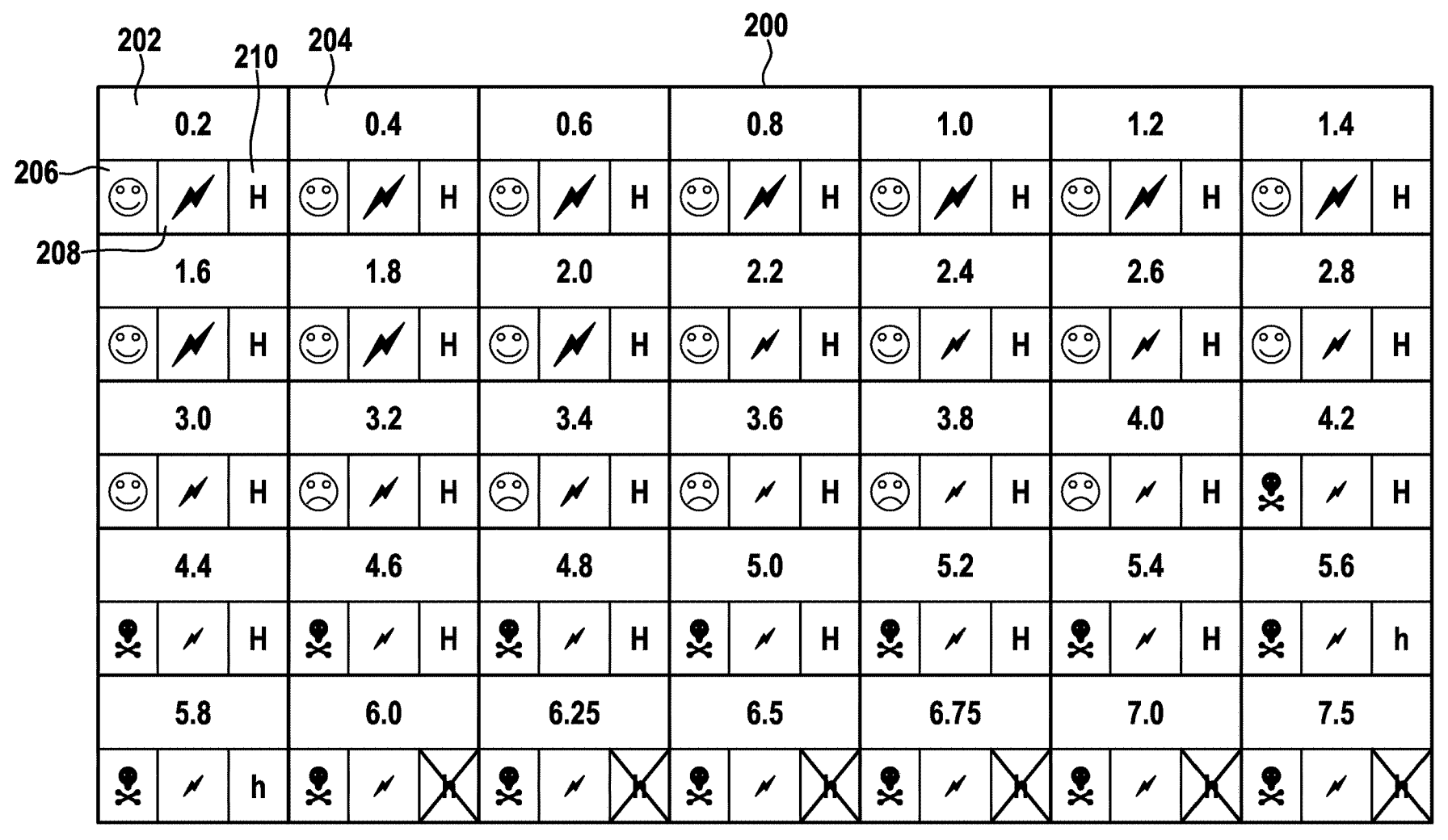

The programming device 150 has a display 152 which displays programming options to a programmer, as exemplified by the menu 200 of stimulation vectors 202, 204, etc. shown in FIG. 2. The stimulation vectors 202, 204, etc.— shown as "0.2," "0.4," etc. (representing pulse amplitudes of 0.2 mA, 0.4 mA, etc.)—are each shown with acceptability indicia provided as a row of three icons. The first icon (at 206) represents a stimulation vector's patient safety margin (e.g., proximity to limits defined by the Shannon criteria), and is depicted by a happy face where a stimulation vector results in high safety margins; by a sad face where a stimulation vector results in low safety margins; and by a danger symbol where a stimulation vector does not meet safety criteria. The second icon (at 208) represents a stimulation vector's impact on electrostimulator battery life, and is depicted by a large lightning bolt where a stimulation vector has low impact on battery life, and by smaller lightning bolts for stimulation vectors having greater impact on battery life. The third icon (at 210) represents the electrostimulator's ability to deliver the stimulation vector, with a large "H" being shown where a stimulation vector can be delivered without difficulty, a smaller "h" being shown where the stimulation vector might be implemented with reconfiguration of the electrostimulator's routines (or with other compromises), and an "X" being shown where the electrostimulator simply cannot accommodate the stimulation vector. A programmer might therefore select a suitable stimulation vector 202, 204, etc., and use the acceptability indicia to make a more well-informed decision on which vector seems optimal.

It should be understood that the display 200 of FIG. 2 is a basic one, and displays can be significantly more complex. For example, the displayed stimulation vectors 202, 204, etc. could show parameters in addition to, or instead of, merely pulse amplitude; for example, each pulse amplitude shown in FIG. 2 might be accompanied by a pulse width/duration. Or, after selecting a suitable pulse amplitude in FIG. 2, the display 200 may then switch to a similar display illustrating a range of pulse widths available for selection with the selected pulse amplitude, and also showing acceptability indicia for each of the available pulse widths. A display might show a menu of all available stimulation vectors, and all of the parameters within each vector, but showing certain stimulation vectors in a different format (e.g., font, case, stylization, size, and/or color) if their status vectors are outside of a desirable range. To illustrate, stimulation vectors having status vectors within safety margins might be shown in green, while those closely approaching patient safety margins, or failing to meet patient safety margins, might be shown in orange to red tones; stimulation vectors having moderate impact on electrostimulator battery life might be shown in bolder type and/or brighter tones, with boldness/brightness decreasing for other stimulation vectors in dependence on their impact on battery life; and stimulation vectors exceeding electrostimulator performance limits might be shown struck through with a line while other stimulation vectors are not.

Figure 3:
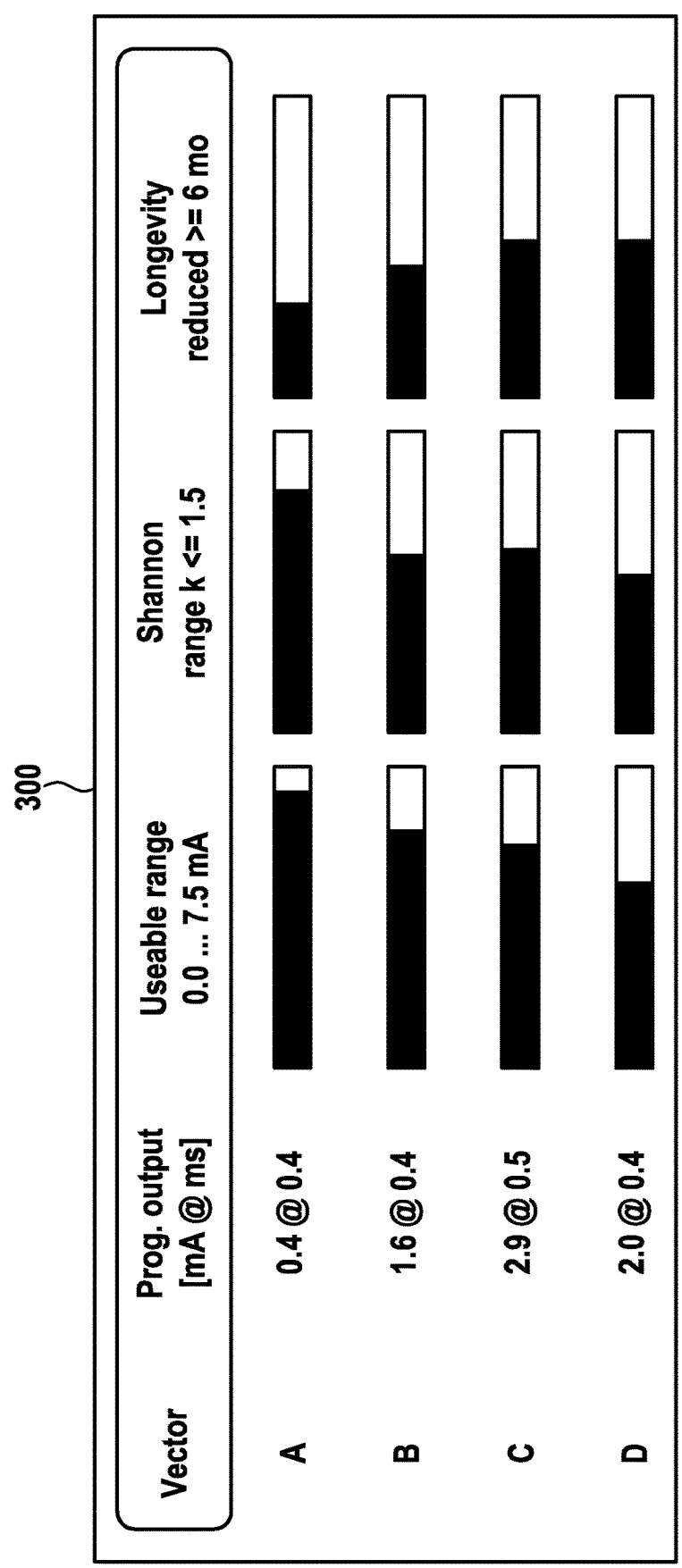
FIG. 3 is a diagram of another simple exemplary graphical user interface (GUI) that might be displayed on the screen of a programming device to allow a programmer to choose a desired stimulation vector.

As discussed above, the programming device 150 need not present the programmer with all possible stimulation vectors, and it could instead present only those stimulation vectors having acceptable status vectors. To illustrate, in the foregoing example, the display might exclude those stimulation vectors having status vectors outside patient safety margins and/or outside electrostimulator performance limits, showing only those stimulation vectors providing safe and workable results (and with their boldness/brightness varying in dependence on their impact on battery life). The exemplary display 300 of FIG. 3 shows a similar arrangement wherein only stimulation vectors having acceptable status vectors are shown, but parameters of their status vectors are shown as well (namely, proximity to hardware capability limits; proximity to patient safety threshold; and impact on battery life). This status vector information allows the programmer to make a more informed choice of stimulation vectors.

Apart from formatting displayed stimulation vectors to better indicate those that are safe, practicable, and/or that support device longevity (or otherwise restricting the displayed stimulation vectors to those that meet these criteria), the invention might also advise of emerging stimulation parameter conflicts, and/or of available ranges of stimulation parameters, in cases where the programmer is selecting individual stimulation parameters within a stimulation vector. As a simple example, consider a situation where a programmer is defining stimulation timing parameters within a stimulation vector, such as stimulation pulse frequency, pulse burst frequency, and pulse quantity per pulse burst. The programmer might, for example, seek to administer bursts of output current having 10 pulses per burst delivered at 1 Hz pulse frequency, with a burst frequency of 80 bursts per minute. These parameters are impossible, as 80 bursts per minute can't be accomplished if each burst contains 10 pulses at a 1 Hz frequency. As a programmer begins selecting the stimulation parameters making up a stimulation vector, the invention might address this by dynamically showing, after the programmer defines each stimulation parameter, the available practical ranges for the remaining stimulation parameters. In this manner, after each stimulation parameter is chosen, the programmer is directed (or restricted) to values of the remaining parameters that are feasible, patient-safe, and device-friendly.

The invention can also provide a programmer with a statistical or other indication of how a change in the selected stimulation vector(s) might affect patient safety and/or comfort, battery and/or device life, and the like. The programmer is therefore given instantaneous feedback on the potential effect of a programming change.

An electrostimulator in accordance with the invention might also incorporate functionality wherein the status vector resulting from a selected stimulation vector, or some range of acceptable status vectors, serve as a benchmark for desired future electrostimulation output behaviors. Deviations from the benchmark during the electrostimulator's operation can be stored in any performance log maintained within the electrostimulator, and/or may be wirelessly or otherwise communicated to remote monitoring systems. Alternatively or additionally, the benchmark might be used as a control parameter for closed-loop modification of the stimulation vector(s) used by the electrostimulator, with patient physiological data possibly serving as an additional feedback variable. Thus, the electrostimulator could automatically adapt its stimulation vector(s) to achieve desired (or at least acceptable) physiological response from the patient, while at the same time achieving desired (or at least acceptable) status vectors.

It should be understood that while the foregoing discussion noted the monitoring of lead impedance and its use in determining status vectors, quantities which are functionally equivalent to lead impedance may be used instead, such as actual current delivered, or tissue resistance. Throughout this document, where reference is made to "lead impedance," this term should be regarded as encompassing these equivalent quantities instead of (or in addition to) lead impedance.

The versions of the invention discussed above are exemplary, and the invention can assume different forms. In particular, the invention can be implemented in different kinds of electrostimulators apart from neurostimulators (e.g., IPGs), for example, to cardiostimulators (e.g., ICDs). The invention is not intended to be limited to the exemplary versions described above, but rather is intended to be limited only by the claims set out below. Thus, the invention encompasses all different versions that fall literally or equivalently within the scope of these claims.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

The invention claimed is:

1. A method of programming a therapeutic electrostimulator, which comprises the steps of:
   delivering electrostimulation to patient tissue via an electrostimulator lead, the electrostimulation being defined by a selected one of several available stimulation vectors;
   measuring a lead impedance of the electrostimulator lead;
   calculating a status vector for each of the several available stimulation vectors, the status vector representing an effect of delivering the electrostimulation;
   i) at a measured lead impedance; and
   ii) using a stimulation vector corresponding to the status vector; and
   displaying at least two of the several available stimulation vectors for selection by a programmer, wherein a display is dependent on at least one acceptability indicator of the status vectors, and wherein each of the several available stimulation vectors having at least two of:
   a stimulation pulse frequency;
   a pulse burst frequency; and
   a pulse quantity per pulse burst;
   storing the status vector resulting from selected stimulation vectors or a range of acceptable status vectors as a benchmark; and
   identifying deviations of calculated status vectors from the benchmark.

2. The method according to claim 1, wherein the step of displaying at least two of the several available stimulation vectors includes displaying only the several available stimulation vectors having acceptable status vectors according to the at least one acceptability indicator.

3. The method according to claim 1, wherein the step of displaying at least two of the several available stimulation vectors includes displaying:
   the several available stimulation vectors having acceptable status vectors;
   the several available stimulation vectors having unacceptable status vectors; and
   the acceptability indicator, the at least one acceptability indicator visually differentiating displayed stimulation vectors having the acceptable status vectors from the displayed stimulation vectors having the unacceptable status vectors.

4. The method according to claim 1, which further comprises displaying the lead impedance.

5. The method according to claim 1, wherein the status vectors include patient safety margins.

6. The method according to claim 1, wherein the status vectors further include electrostimulator battery life.

7. The method according to claim 1, wherein the status vectors further include electrostimulator performance limits.

8. The method according to claim 1, wherein each of the several available stimulation vectors includes a stimulation pulse amplitude and a stimulation pulse width.

9. The method according to claim 1, which further comprises repeating the steps of claim 1, whereby the display is updated to reflect effects of changes in the measured lead impedance.

10. The method according to claim 1, which further comprises storing identified deviations in a memory maintained within the therapeutic electrostimulator, and/or communicating the identified deviations to remote monitoring systems.

11. The method according to claim 1, which further comprises using the benchmark as a control parameter for modification of the several available stimulation vectors used by the therapeutic electrostimulator in a closed-loop manner.

12. The method according to claim 1, which further comprises providing a programmer with a statistical indication of how a change in a selected stimulation vector might affect patient safety, patient comfort, battery life, or device life.

13. The method according to claim 1, which further comprises providing a programmer h notice of emerging stimulation parameter conflicts within a selected stimulation vector.

14. A method of programming a therapeutic electrostimulator, the therapeutic electrostimulator having a lead with an electrode thereon, a battery, and a controller configured to deliver electrostimulation from the battery to patient tissue via the electrode, delivered electrostimulation being defined by a selected one of several available stimulation vectors, the method including the steps of:
    measuring lead impedance;
    calculating a status vector for each of the several available stimulation vectors, the status vector being indicative of an effect of delivering the electrostimulation:
        i. using a corresponding stimulation vector; and
        ii. at a measured lead impedance; and
    visually displaying at least two of the several available stimulation vectors for selection by a programmer, wherein a visible appearance of a display is dependent on at least one acceptability indicator of the status vectors, and wherein each of the several available stimulation vectors having at least two of:
        a stimulation pulse frequency;
        a pulse burst frequency; and
        a pulse quantity per pulse burst;
    storing the status vector resulting from selected stimulation vectors or a range of acceptable status vectors as a benchmark; and
    identifying deviations of calculated status vectors from the benchmark.

15. The method according to claim 14, wherein the status vectors include at least one of:
    patient safety margins;
    electrostimulator battery life; and
    electrostimulator performance limits.

16. The method according to claim 14, wherein each of the several available stimulation vectors includes a stimulation pulse amplitude and a stimulation pulse width.

17. The method according to claim 14, further including the step of visually displaying a representation of the measured lead impedance simultaneously with the display of the several available stimulation vectors.

18. The method according to claim 14, wherein the step of displaying at least two of the several available stimulation vectors includes displaying only the several available stimulation vectors having acceptable status vectors according to the at least one acceptability indicator.

19. The method according to claim 14, wherein the step of displaying at least two of the several available stimulation vectors includes displaying:
    the several available stimulation vectors having acceptable status vectors;
    the several available stimulation vectors having unacceptable status vectors; and
    the acceptability indicator, the at least one acceptability indicator visually differentiating displayed stimulation vectors having the acceptable status vectors from the displayed stimulation vectors having the unacceptable status vectors.

* * * * *